(12) United States Patent
Kawai et al.

(10) Patent No.: US 6,602,663 B1
(45) Date of Patent: Aug. 5, 2003

(54) METHOD FOR DETECTION OR MEASURING PLASMOCYTOMA CELLS

(75) Inventors: Shigeto Kawai, Gotemba (JP); Yasuo Koishibara, Gotemba (JP); Masaaki Kosaka, Tokushima (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/787,375

(22) PCT Filed: Aug. 20, 1999

(86) PCT No.: PCT/JP99/04502

§ 371 (c)(1),
(2), (4) Date: Mar. 16, 2001

(87) PCT Pub. No.: WO00/17395

PCT Pub. Date: Mar. 30, 2000

(30) Foreign Application Priority Data

Sep. 18, 1998 (JP) .............................. 10-264593

(51) Int. Cl.[7] .......................... C12Q 1/68; C12P 19/34; C07H 21/04
(52) U.S. Cl. ........................ 435/6; 435/91.2; 536/23.1; 536/24.3
(58) Field of Search .................... 435/6, 91.2; 536/24.3, 536/23.1

(56) References Cited

FOREIGN PATENT DOCUMENTS

| | | |
|---|---|---|
| EP | 0 960 936 | 12/1999 |
| JP | 10-155494 | 6/1998 |

OTHER PUBLICATIONS

Billadeau, D. et al., "Detection and Quantitation of Malignant Cells in the Peripheral Blood of Multiple Myeloma Patients", Blood, vol. 80, pp. 1818–1824 (1992).*
Goto, T. et al., "A Novel Membrane Antigen Selectively Expressed on Terminally Differentiated Human B Cells", Blood, vol. 84, pp. 1922–1930 (1994).*
Anderson et al., "Antigens on Human Plasma Cells Identified by Monoclonal Antibodies", *The Journal of Immunology*, Mar. 1983, vol. 130, No. 3, pp. 1132–1138, The American Association of Immunologists.
Anderson et al., "A Monoclonal Antibody with Reactivity Restricted to Normal and Neoplastic Plasma Cells", *The Journal of Immunology*, Jun. 1984, vol. 132, No. 6, pp. 3172–3179, The American Association of Immunologists.
Tong et al., "Characterization of a Monoclonal Antibody Having Selective Reactivity with Normal and Neoplastic Plasma Cells", *Blood*, Jan. 1987, vol. 69, No. 1, p. 238–245, Grune & Stratton, Inc.

Epstein et al., "Markers of Multiple Hematopoietic–Cell Lineages In Multiple Myeloma", *The New England Journal of Medicine*, Mar. 8, 1990, vol. 322, No. 10, pp. 664–668.
Terstappen et al., "Identification and Characterization of Plasma Cells In Normal Human Bone Marrow by High–Resolution Flow Cytometry", *Blood*, Nov. 1, 1990, vol. 76, No. 9, pp. 1739–1747, The American Society of Hematology.
Leo et al., "Multiparameter Analyses of Normal and Malignant Human Plasma Cells: CD38++, CD56+, CD54+, cIg+ is the Common Phenotype of Myeloma Cells" *Hematology*, 1992, vol. 64, pp. 132–139, Springer–Verlag.
Shimazaki et al., "Immunophenotype and DNA Content of Myeloma Cells in Primary Plasma Cell Leukemia", *American Journal of Hematology*, 1992, vol. 39, pp. 159–162, Wiley–Liss, Inc.
Hata et al., "Interleukin–6 Gene Expression in Multiple Myeloma: A Characteristic of Immature Tumor Cells", *Blood*, Jun. 15, 1993, vol. 81, No. 12, pp. 3357–3364, The American Society of Hematology.
Harada et al., "Phenotypic Difference of Normal Plasma Cells From Mature Myeloma Cells", *Blood*, May 15, 1993, vol. 81, No., 10, pp. 2658–2663, The American Society of Hematology.
Billadeau et al., "The Bone Marrow of Multiple Myeloma Patients Contains B Cell Populations at Different Stages of Differentiation That Are Clonally Related to the Malignant Plasma Cell", *J. Exp. Med.*, Sep. 1993, vol. 178, pp. 1023–1031, The Rockefeller University.
Goto et al., "A Novel Membrane Antigen Selectively Expressed on Terminally Differentiated Human B Cells", *Blood*, Sep. 15, 1994, vol. 84, No. 6, pp. 1922–1930, The American Society of Hematology.
Jpn. J. Clin. Immun., 1992, vol. 16, in Japanese with English Summary, pp. 688–691.
Corradinin P. et al., "High–Dose Sequential Chemoradiotherapy in Multiple Myeloma:Residual Tumor Cells Are Detectable in Bone Marrow and Peripheral Blood Cell harvests and After Autografting", Blood (1995) vol. 85, No. 6, pp. 1596–1602, The American Society of Hematology.

* cited by examiner

*Primary Examiner*—Kenneth R. Horlick
*Assistant Examiner*—Teresa Strzelecka
(74) *Attorney, Agent, or Firm*—Foley & Lardner

(57) ABSTRACT

A method of detecting or determining plasmacytoma cells in a sample, said method comprising amplifying a polynucleotide that is specifically or strongly expressed in said plasmacytoma cells, and then detecting or measuring the amplified product.

9 Claims, No Drawings

METHOD FOR DETECTION OR MEASURING PLASMOCYTOMA CELLS

TECHNICAL FIELD

The present invention relates to methods for detecting and measuring plasmacytoma cells in a sample.

BACKGROUND ART

Plasmacytoma, represented by multiple myeloma, is generally termed a myeloma, and is pathologically divided into multiple myeloma, plasma cell leukemia, solitary plasmacytoma, extramedullary plasmacytoma, smoldering multiple myeloma, or asymptomatic myeloma. All of them are B cell tumors and are characterized by abnormal growth of monoclonal plasma cells (antibody-producing cells). Many of these tumors accumulate in the bone marrow and are diseases of poor prognosis accompanied by systemic bone lesions.

In multiple myeloma, terminally differentiated B cells or plasma cells that produce and secrete immunoglobulins monoclonally increase predominantly in the bone marrow, and thereby monoclonal immunoglobulins (M proteins) or their constituent light chains and/or H chains are detected in the blood and urine. With the aging of the population in recent years, patients with multiple myeloma are growing in number, and the mortality rate has reached 2.1 in 100,000 people in Japan.

The diagnosis of multiple myeloma has been made based on the detection of M proteins and/or bone lesions. These methods, however, required that the number of myeloma cells to be detected amounted to 0.2 to $1.2 \times 10^{12}$, systemically, and even for the detection of M proteins, growth of myeloma cells to about $1.2 \times 10^{10}$ was required. This rendered the early detection thereof difficult.

Furthermore, since these methods of diagnosis do not always reflect the amount of tumor cells, it was inconveniently impossible to decide effective regimens for treatment. In addition, it was also difficult to differentiate from benign monoclonal immunoglobulinemia in which M proteins are similarly detected, or to diagnose the non-secretory type myeloma in which no M proteins are present.

On the other hand, there have been attempts to diagnose myeloma using antibodies that recognize antigen on the cell membrane of plasma cells. These antibodies include such monoclonal antibodies as anti-PCA-1 (Anderson, K. C. et al., J. Immunol. (1983) 130, 1132), anti-PC-1 (Anderson, K. C. et al., J. Immunol. (1983) 132, 3172), anti-MM4 (Tong, A. W. et al., Blood (1987) 69, 238), anti-CD38 (Epstein, J. et al., N. Eng. J. Med. (1990) 322, 664, Terstappen, L. W. M. M. et al., Blood (1990) 76, 1739, Leo, R. et al., Ann. Hematol. (1992) 64, 132, Shimazaki, C. et al., Am. J. Hematol. (1992) 39, 159, Hata, H. et al., Blood (1993) 81, 3357, Harada, H. et al., Blood (1993) 81, 2658, Billadedeau, D. et al., J. Exp. Med. (1993) 178, 1023) and the like. Since such detection using antibody required a sample that contained a large amount of myeloma cells, it was particularly unsuitable for early detection in which myeloma cells were not always present.

On the other hand, Goto, T. et al. reported that they immunized mice with human plasma cells and obtained a mouse monoclonal anti-HM1.24 antibody that recognizes an antigen having a molecular weight of 29–33 kDa specifically expressed on B cell lines (Blood (1994) 84, 1922). It was further reported that the antigen (HM1.24) recognized by monoclonal anti-HM1.24 antibody is considered to be an antigen associated with the terminal differentiation of B cells (Goto, T. et al., Jpn. J. Clin. Immun. (1992) 16, 688), and that monoclonal anti-HM1.24 antibody reacts to plasmacytoma in a specific manner (Shuji Ozaki et al., the program of The 19th General Meeting of Japan Myeloma Study Group, General presentation 3). It was not known, however, that the diagnosis of plasmacytoma could be effected using the gene of HM1.24.

DISCLOSURE OF THE INVENTION

It is an object of the present invention to provide a method that permits a simple and sensitive detection or measurement even with a small amount of tumor cells, and that permits the diagnosis of plasmacytoma.

In order to attain the above object, the present inventors have devised a combination of primers and a probe based on the already-known sequence of the HM1.24 gene (Japanese Patent Application No. 9-271536), attempted to detect and measure the amount expressed of HM1.24 mRNA in a simple and sensitive manner and to quantitate the amount expressed. As a result of intensive research, the present inventors have found that plasmacytoma cells can be specifically detected or measured by PCR-amplifying HM1.24 mRNA from a small amount of tumor cells and using a probe labeled with fluorescence, and that plasmacytoma can be diagnosed by amplifying similarly normal cells or tumor cells other than plasmacytoma cells as a control sample and then comparing the amount of the amplified product, and thereby have completed the present invention.

Thus, the present invention provides a method of detecting or determining plasmacytoma cells in a sample, said method comprising amplifying a polynucleotide that is specifically or strongly expressed in plasmacytoma cells and then detecting or measuring the amplified product.

As said plasmacytoma, there can be mentioned multiple myeloma, plasma cell leukemia, solitary plasmacytoma, extramedullary plasmacytoma, smoldering multiple myeloma, asymptomatic myeloma and the like.

Preferably, said polynucleotide is DNA or mRNA, in particular mRNA, that encodes the HM1.24 antigen.

Preferably, said amplification method is the PCR method.

Preferably, said measurement method is a method that employs a labeled probe.

Preferably, said label is a fluorophore, a radioisotope, an enzyme or a combination thereof.

The present invention also provides a method of diagnosing plasmacytoma by detecting or measuring plasmacytoma cells in a sample, said method comprising amplifying a polynucleotide that is specifically or strongly expressed in said plasmacytoma cells, detecting or measuring the amplified product, and then comparing the amount of the amplified product to that in a control sample.

EMBODIMENT FOR CARRYING OUT THE INVENTION

Plasmacytoma that is the subject of the detection or measurement method of the present invention is a tumor that expresses the HM1.24 antigen having the amino acid sequence as set forth in SEQ ID NO: 1 or the amino acid sequence substantially identical to said amino acid sequence, and includes multiple myeloma, plasma cell leukemia, solitary plasmacytoma, extramedullary plasmacytoma, smoldering multiple myeloma, asymptomatic myeloma and the like.

Samples containing plasmacytoma cells may be prepared by isolating leukocytes from the peripheral blood or the bone marrow of patients with plasmacytoma and collecting RNA therefrom. Since many of the myelomas tend to form a tumor mass in the bone marrow, it is desirable to collect leukocytes containing plasmacytoma cells by the bone marrow puncture to said tumor mass. In cases where there is a marked appearance of tumor cells in the peripheral blood as in plasma cell leukemia etc., the use of peripheral blood is preferred because of simplicity in handling.

In order to isolate leukocytes containing plasmacytoma cells from the peripheral blood or the bone marrow collected from patients with plasmacytoma, a commercially available reagent may be used for separation by gradient centrifugation. As the commercially available reagent, there can be used Ficoll-Paque (manufactured by PHARMACIA BIOTECH), a Mono-Poly Resolving Medium (manufactured by Dainippon Pharmaceuticals), and the like. It is also possible to prepare leukocytes by lysing red blood cells in a hypotonic buffer and then washing by centrifugation. As a solution used in washing, there can be used isotonic solutions such as PBS and MEM.

In order to prepare RNA from the thus obtained leukocytes, a method well known to those skilled in the art may be used (see, for example, Idensi Sousa Jikkenhou (Experiments on Genetic Manipulation), Yasutaka Takagi, Kodansha Scientific, pp. 24–39, 1980). RNA may be total RNA or mRNA. Total RNA or mRNA can be extracted using a commercially available kit, for example TRIZOL (manufactured by GIBCO BRL), ISOGEN (manufactured by Wako Pure Chemicals Industries, Ltd.), and mRNA Purification Kit (manufactured by PHARMACIA BIOTECH).

Any target polynucleotide can be used as long as it is specifically or strongly expressed in plasmacytoma cells. However, due to ease of detection, it is preferably DNA or mRNA, in particular mRNA, encoding the HM1.24 antigen that is specifically expressed in plasmacytoma cells.

In accordance with the present invention, a specific example of a strongly expressed polynucleotide includes a polynucleotide that is expressed five-fold or more, preferably 10-fold or more, and most preferably 20-fold or more than normal cells or tumor cells other than plasmauytoma cells.

A relative amount of the polynucleotide expressed in a sample may be determined by subjecting RNA or mRNA extracted from said cells to agarose gel electrophoresis, allowing the product to be adsorbed to a membrane, performing Northern blot hybridization using a radio-labeled probe, and then determining and comparing the radioactivity. Alternatively, the competitive RT-PCR method (Competitive RNA Transcription Kit, Takara) may be used to amplify, at the same time, the RNA competitor and the mRNA of interest in the same reaction mixture with the same primer. Then, based on the ratio of the amplified products, the original amount of mRNA can be estimated. Furthermore, it can be simply determined using ABI PRISM7700 according to the method described in Examples.

As the method of amplification, the PCR method (polymerase chain reaction method) can be used. When the polynucleotide of interest is mRNA, the use of RT-PCR is preferred. For the PCR method or the RT-PCR method, a commercially available reagent may be used including the TaKaRa RNA LA PCR™ Kit (AMV) Ver 1.1 (manufactured by Takara Shuzo), the RT-PCR high-Plus-(manufactured by Toyoboseki), or the TaqMan EZ RT-PCR Kit (manufactured by Perkin-Elmer) and the like.

As a method of amplification, in addition to the PCR method, the TMA method (Transcription Mediated Amplification method: Japanese PCT Publication No. 4-500759) that amplifies RNA may be used.

The primer is a pair of oligonucleotides that can amplify a segment of the nucleotide sequence as set forth in SEQ ID NO: 1, specifically a pair of oligonucleotides that can hybridize, at a certain interval, to a nucleic acid having the nucleotide sequence as set forth in SEQ ID NO: 1 or a nucleic acid complementary thereto. The distance on the sequence of SEQ ID NO: 1 to which the pair of oligonucleotides hybridize is, but is not limited to, a range of 30 to 400 nucleotides, preferably 50 to 200 nucleotides.

The primer is preferably selected from the region in which the amino acid sequence is well conserved among the species and mainly in the extracellular region from positions 48 to 124 in the amino acid sequence of SEQ ID NO: 1.

Based on the above conditions, the primer can be selected using, for example, a commercially available analytic al software such as Primer Express (manufactured by Perkin-Elmer).

The length of the primer to be used for amplification is, but is not limited to, 10 to 100 nucleotides, preferably 10 to 50 nucleotides, more preferably 15 to 30 nucleotides, and more preferably 20 to 25 nucleotides, for example about 20 nucleotides.

Specific examples of such a primer pair include the forward primer (SEQ ID NO: 3) (corresponding to positions 153 to 172 in the nucleotide sequence as set forth in SEQ ID NO: 1) and the reverse primer (SEQ ID NO: 4) (corresponding to positions 304 to 323 in the nucleotide sequence as set forth in SEQ ID NO: 1).

The probe is an oligonucleotide that specifically hybridizes to a nucleotide sequence defined by said one pair of primers. Thus, such a probe is selected from the region between the forward primer and the reverse primer. Though the positions on SEQ ID NO: 1 corresponding to the probe depend on the sites to which the primer pair hybridizes, those that hybridize to the region of nucleotide number 173 to 303 in SEQ ID NO: 1, preferably the region of nucleotide number 224 to 249 are preferred. The length of the probe to be used is, but is not limited to, 10 to 200 nucleotides, preferably 20 to 100 nucleotides, for example 25 to 50 nucleotides, for example about 30 nucleotides.

The amplified polynucleotide can be detected or measured by subjecting the PCR reaction mixture to agarose gel electrophoresis in the presence of a luminescent substance such as ethidium bromide and then measuring the light emitted by said band. When a probe is used, the polynucleotide is detected by allowing it to be adsorbed to a nitrocellulose membrane followed by hybridization to the labeled probe. The sequence or the length of the probe is not limited as long as it can specifically detect the target polynucleotide to be detected.

For labeling, a fluorogenic substance, a radioisotope, an enzyme or a combination thereof may be used. As the fluorogenic substance, FAM (6-carboxyfluorescein), JOE (6-carboxy-4,5-dichloro-2,7-dimethoxyfluorescein), TET (6-carboxy-4,7,2',7'-tetrachlorofluorescein), and HEX (6-carboxy-4,7,2',4',5',7'-hexachlorofluorescein) may be used. As the radioisotope, $^{32}P$ may be used.

As the enzyme, alkaline phosphatase may be used, and as the substrate for the enzyme, CDP-Star™ (manufactured by BOEHRINGER MANNHEIM), for example, may be used. By using ABI PRISM7700 developed by Perkin-Elmer that permits the determination of the product with time while performing the PCR reaction, simple determination can be attained. As the reagent for RT-PCR in this case, TaqMan EZ RT-PCR Kit (manufactured by Perkin-Elmer) is preferably used.

EXAMPLES

The present invention will now be explained in further detail with reference to the following examples.

Example 1

Myeloma cell line U266B1 (ATCC TIB-196), KPMM2 (Deposit number P-14170, Patent application No.: Japanese Patent Application No. 6–58082), ARH-77 (ATCC CRL 1621), RPMI8226 (ATCC CCL 155), and, as other tumor cell lines, a T cell leukemia cell line HPB-ALL (FCCH1018) and a lung cancer cell line A549 (ATCC CCL-185) were used.

Cells ($5 \times 10^6$) of each tumor cell line were centrifuged to prepare pellets, which were suspended in 1 ml of TRIZOL (manufactured by GIBCO BRL) and then allowed to stand at room temperature for 5 minutes. 0.2 ml of chloroform was added thereto, which was vigorously shaken for 15 seconds, allowed to stand at room temperature for 2 minutes, and then centrifuged at 12000×g at 4° C. for 15 minutes. After centrifugation, 0.5 ml of the upper layer of the solution separated into two layers was collected and an equal amount of isopropyl alcohol was added thereto. After shaking and allowing to stand at room temperature for 10 minutes, it was centrifuged at 12000×g at 4° C. for 10 minutes. The precipitate thus obtained was washed with 1 ml of 75% ethanol and then centrifuged at 12000×g at 4° C. for 5 minutes. After drying the precipitate, it was dissolved in 0.1 ml of a DEPC-treated water to collect RNA. The RNA concentration was determined from the absorbance at 260nm.

The sequences of the RT-PCR primer and the probe for specific amplification and detection of HM1.24 mRNA were determined using an analytical software, Primer Express (manufactured by Perkin-Elmer). As a result, 5'-TCACCATCAAGGCCAACAGC-3' (SEQ ID NO: 3) as the forward primer and 5'-AAGCCATTAGGGCCATCACA-3' (SEQ ID NO: 4) as the reverse primer were selected. The production of these primers was referred to Amersham Pharmacia Biotech, and the product was prepared to 0.01 mM in the TE buffer. As the probe, 5'-CATCTCCTGCAACAAGAGCTGACCGA-3' (SEQ ID NO: 5) that bound to a fluorescent dye FAM was used and its production was referred to Perkin-Elmer.

Using the TaqMan EZ RT-PCR Kit (manufactured by Perkin-Elmer) as a reagent for RT-PCR, RT-PCR was performed using ABI PRISM7700 (manufactured by Perkin-Elmer). The PCR comprised 40 cycles. Each specimen was determined in triplicate wells at an amount of 25 microliters per well. The solution was prepared according to the instruction manual of the TaqMan EZ RT-PCR Kit.

Using equal amounts of RNA extracted from each cell line, RT-PCR was performed for 40 cycles, and the amount of fluorescence was simultaneously determined at each step. In this case, the threshold value was set at 0.05, and the number of cycle at which fluorescence intensity exceeds 0.05 was determined for each cell. Preparing a dilution series for RNA extracted from the U266B1 cell line and was plotted with respect to the cycle number and the RNA amount, a good standard curve was obtained at a range of 200 to 0.32 ng. The cycle number for each cell was fitted to the standard curve to calculate a relative value to the amount expressed of HM1.24 mRNA for the U266B1 cell line.

Thus, the amount expressed of HM1.24 mRNA for each cell was calculated based on the amount of HM1.24 mRNA for the U266B1 cell line, and the amount expressed of HM1.24 mRNA for the U266B1 cell line set as one unit. In quantitation, in order to correct for variation in the amount of RNA used in RT-PCR among cell lines, the amount amplified of GAPDH mRNA was simultaneously measured using TaqMan,GAPDH Control Reagents attached to the TaqMan EZ RT-PCR Kit, which was used for correction assuming that an equal amount of GAPDH mRNA is present in the sample.

As a result, the amount of HM1.24 mRNA per cell was calculated as KPMM2=0.921, ARH-77=0.567, RPMI8226= 0.636, U266B1=1.000, HPB-ALL=0.033 and A549=0.000.

From the foregoing, little or no expression was observed in the cells other than the multiple myeloma cells. In contrast, an expression as high as 0.5 to 1 unit was observed for the plasmacytoma cell line indicating that plasmacytoma can be diagnosed using the method of the present invention. The result also indicates that a contamination of $10^4$ myeloma cells per $10^6$ cells can be detected.

What is claimed is:

1. A method of detecting or measuring plasmacytoma cells in a sample, said method comprising amplifying DNA or mRNA that encodes the HM1.24 antigen, and then detecting or measuring the amplified product.

2. The method according to claim 1 wherein said plasmacytoma is multiple myeloma, plasma cell leukemia, solitary plasmacytoma, extramedullary plasmacytoma, smoldering multiple myeloma, or asymptomatic myeloma.

3. The method according to claim 1 wherein said method of amplification is the PCR method.

4. The method according to any of claims 1, 2 or 3 wherein said method of detecting or measuring employs a labeled probe.

5. The method according to claim 4 wherein said label is selected from the group consisting of a fluorophore, a radioisotope, an enzyme and a combination thereof.

6. A method of diagnosing plasmacytoma by detecting or measuring plasmacytoma cells in a sample said method comprising amplifying DNA or mRNA that encodes the HM1.24 antigen, detecting or measuring the amplified product, and then comparing the amount of the amplified product to that in a control sample.

7. The method according to claim 2 wherein said method of amplification is the PCR method.

8. The method according to claim 2 wherein said method of detecting or measuring employs a labeled probe.

9. The method according to claim 3 wherein said method of detecting or measuring employs a labeled probe.

* * * * *

SEQUENCE LISTING

<160> NUMBER OF SEQ ID NOS: 5

<210> SEQ ID NO 1
<211> LENGTH: 1013
<212> TYPE: DNA
<213> ORGANISM: Homo sapiens
<220> FEATURE:
<221> NAME/KEY: CDS
<222> LOCATION: (23)..(562)
<223> OTHER INFORMATION: DNA coding for HM1.24 antigen protein

<400> SEQUENCE: 1

```
gaattcggca cgagggatct gg atg gca tct act tcg tat gac tat tgc aga        52
                       Met Ala Ser Thr Ser Tyr Asp Tyr Cys Arg
                        1               5                  10
```

-continued

| | |
|---|---|
| gtg ccc atg gaa gac ggg gat aag cgc tgt aag ctt ctg ctg ggg ata<br>Val Pro Met Glu Asp Gly Asp Lys Arg Cys Lys Leu Leu Leu Gly Ile<br>                  15                        20                        25 | 100 |
| gga att ctg gtg ctc ctg atc atc gtg att ctg ggg gtg ccc ttg att<br>Gly Ile Leu Val Leu Leu Ile Ile Val Ile Leu Gly Val Pro Leu Ile<br>                30                      35                        40 | 148 |
| atc ttc acc atc aag gcc aac agc gag gcc tgc cgg gac ggc ctt cgg<br>Ile Phe Thr Ile Lys Ala Asn Ser Glu Ala Cys Arg Asp Gly Leu Arg<br>            45                        50                        55 | 196 |
| gca gtg atg gag tgt cgc aat gtc acc cat ctc ctg caa caa gag ctg<br>Ala Val Met Glu Cys Arg Asn Val Thr His Leu Leu Gln Gln Glu Leu<br>60                        65                        70 | 244 |
| acc gag gcc cag aag ggc ttt cag gat gtg gag gcc cag gcc gcc acc<br>Thr Glu Ala Gln Lys Gly Phe Gln Asp Val Glu Ala Gln Ala Ala Thr<br>75                        80                        85                        90 | 292 |
| tgc aac cac act gtg atg gcc cta atg gct tcc ctg gat gca gag aag<br>Cys Asn His Thr Val Met Ala Leu Met Ala Ser Leu Asp Ala Glu Lys<br>                95                      100                      105 | 340 |
| gcc caa gga caa aag aaa gtg gag gag ctt gag gga gag atc act aca<br>Ala Gln Gly Gln Lys Lys Val Glu Glu Leu Glu Gly Glu Ile Thr Thr<br>            110                      115                      120 | 388 |
| tta aac cat aag ctt cag gac gcg tct gca gag gtg gag cga ctg aga<br>Leu Asn His Lys Leu Gln Asp Ala Ser Ala Glu Val Glu Arg Leu Arg<br>            125                      130                      135 | 436 |
| aga gaa aac cag gtc tta agc gtg aga atc gcg gac aag aag tac tac<br>Arg Glu Asn Gln Val Leu Ser Val Arg Ile Ala Asp Lys Lys Tyr Tyr<br>140                        145                        150 | 484 |
| ccc agc tcc cag gac tcc agc tcc gct gcg gcg ccc cag ctg ctg att<br>Pro Ser Ser Gln Asp Ser Ser Ser Ala Ala Ala Pro Gln Leu Leu Ile<br>155                        160                      165                      170 | 532 |
| gtg ctg ctg ggc ctc agc gct ctg ctg cag tgagatccca ggaagctggc<br>Val Leu Leu Gly Leu Ser Ala Leu Leu Gln<br>                  175                      180 | 582 |
| acatcttgga aggtccgtcc tgctcggctt tcgcttgaa cattcccttg atctcatcag | 642 |
| ttctgagcgg gtcatggggc aacacggtta gcggggagag cacggggtag ccggagaagg | 702 |
| gcctctggag caggtctgga ggggccatgg ggcagtcctg ggtctgggga cacagtcggg | 762 |
| ttgacccagg gctgtctccc tccagagcct ccctccggac aatgagtccc cctcttgtc | 822 |
| tcccaccctg agattgggca tggggtgcgg tgtgggggc atgtgctgcc tgttgttatg | 882 |
| ggttttttt gcgggggggg ttgcttttttt ctgggtgtct tgagctccaa aaaataaac | 942 |
| acttcctttg agggagagca caccttaaaa aaaaaaaaa aaaaaaaaa aaaaaattc | 1002 |
| gggcggccgc c | 1013 |

<210> SEQ ID NO 2
<211> LENGTH: 180
<212> TYPE: PRT
<213> ORGANISM: Homo sapiens
<220> FEATURE:
<223> OTHER INFORMATION: Amino acid sequence of HM1.24 antibody protein

<400> SEQUENCE: 2

Met Ala Ser Thr Ser Tyr Asp Tyr Cys Arg Val Pro Met Glu Asp Gly
1                5                          10                          15

Asp Lys Arg Cys Lys Leu Leu Leu Gly Ile Gly Ile Leu Val Leu Leu
                  20                        25                        30

Ile Ile Val Ile Leu Gly Val Pro Leu Ile Ile Phe Thr Ile Lys Ala
                  35                        40                        45

```
Asn Ser Glu Ala Cys Arg Asp Gly Leu Arg Ala Val Met Glu Cys Arg
    50                  55                  60

Asn Val Thr His Leu Leu Gln Gln Glu Leu Thr Glu Ala Gln Lys Gly
 65                  70                  75                  80

Phe Gln Asp Val Glu Ala Gln Ala Ala Thr Cys Asn His Thr Val Met
                 85                  90                  95

Ala Leu Met Ala Ser Leu Asp Ala Glu Lys Ala Gln Gly Gln Lys Lys
                100                 105                 110

Val Glu Glu Leu Glu Gly Glu Ile Thr Thr Leu Asn His Lys Leu Gln
            115                 120                 125

Asp Ala Ser Ala Glu Val Glu Arg Leu Arg Arg Glu Asn Gln Val Leu
        130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Forward
      primer for amplifying a part of DNA coding for HM1.24 antibody
      protein

<400> SEQUENCE: 3
tcaccatcaa ggccaacagc                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Reverse
      primer for amplifying a part of HM1.24 antibody protein

<400> SEQUENCE: 4
aagccattag ggccatcaca                                                      20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Probe for
      detecting an amplification product by SEQ ID NOS 3 and 4

<400> SEQUENCE: 5
catctcctgc aacaagagct gaccga                                               26
```